United States Patent [19]

Schumacher

[11] Patent Number: 4,900,723
[45] Date of Patent: Feb. 13, 1990

[54] METHOD OF PREVENTING OR REDUCING VENOUS THROMBOSIS USING A THROMBOXANE A₂ RECEPTOR ANTAGONIST IN CONJUNCTION WITH HEPARIN AND COMBINATION

[75] Inventor: William A. Schumacher, Newtown, Pa.

[73] Assignee: E. R. Squibb & Sons, Inc., Princeton, N.J.

[21] Appl. No.: 188,571

[22] Filed: Apr. 29, 1988

[51] Int. Cl.⁴ .................. A01N 43/04; C08B 37/10; C12Q 1/56; G01N 33/86
[52] U.S. Cl. ........................... 514/56; 536/21; 435/13; 436/69
[58] Field of Search ............... 514/56; 536/21; 435/13; 436/69

[56] References Cited

U.S. PATENT DOCUMENTS

| | | | |
|---|---|---|---|
| 4,687,865 | 8/1987 | Thottathil | 548/229 |
| 4,689,323 | 8/1987 | Mitra et al. | 514/56 |
| 4,782,026 | 11/1988 | Baugh et al. | 435/13 |

OTHER PUBLICATIONS

Comerota et al., "Combined dihydroergotamine and heparin prophylaxis of postoperative deep vein thrombosis; proposed mechanism of action," Am. J. Surgery 150: 39–44, 1985.
Hampson et al., "Failure of low-dose heparin to prevent deep-vein thrombosis after hip-replacement arthroplasty," Lancet 2:795–797, 1985.
Kakkar et al., "Prophylaxis for postoperative deep-vein thrombosis," JAMA 241:39–42, 1979.
Vinazzer et al., "Prophylaxis of postoperative thromboembolism by low dose heparin and by acetylsalicyclic acid given simultaneously, A double blind study," Throm. Res. 17:177–184, 1980.
Yett et al., "The hazards of aspirin plus heparin," New Eng. J. Med. 298:1092, 1978.
Barrowcliffe et al., "Procoagulant activity of arachidonic acid metabolites," Br. J. Pharmacol, 92:129–132, 1987.
Jennings, J. J. et al., J. Bone Joint Surgery, 58A:9-26–928, 1976.

Primary Examiner—Ronald W. Griffin
Assistant Examiner—Everett White
Attorney, Agent, or Firm—Burton Rodney

[57] ABSTRACT

A method is provided for preventing or reducing deep vein thrombosis and/or pulmonary embolism by administering a thromboxane A₂ receptor antagonist in conjunction with heparin. A combination of thromboxane A₂ receptor antagonist and heparin is also provided.

20 Claims, 1 Drawing Sheet

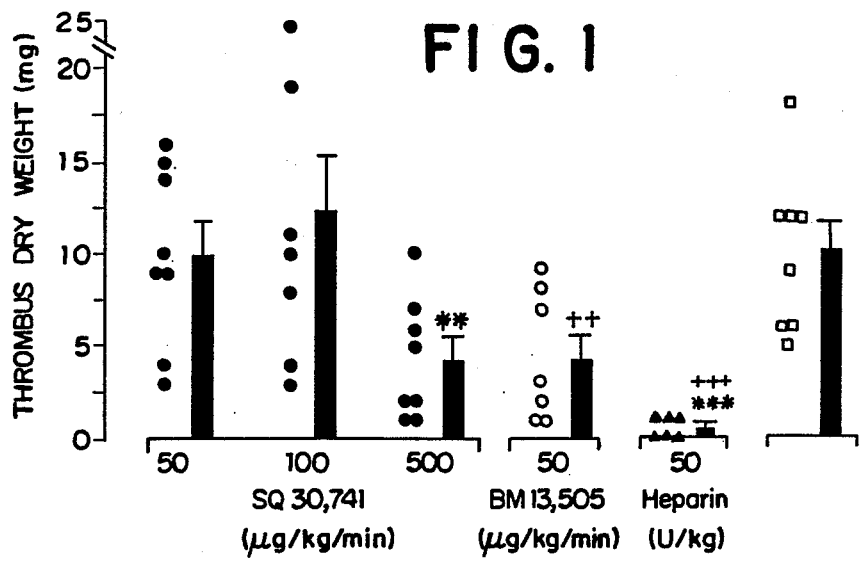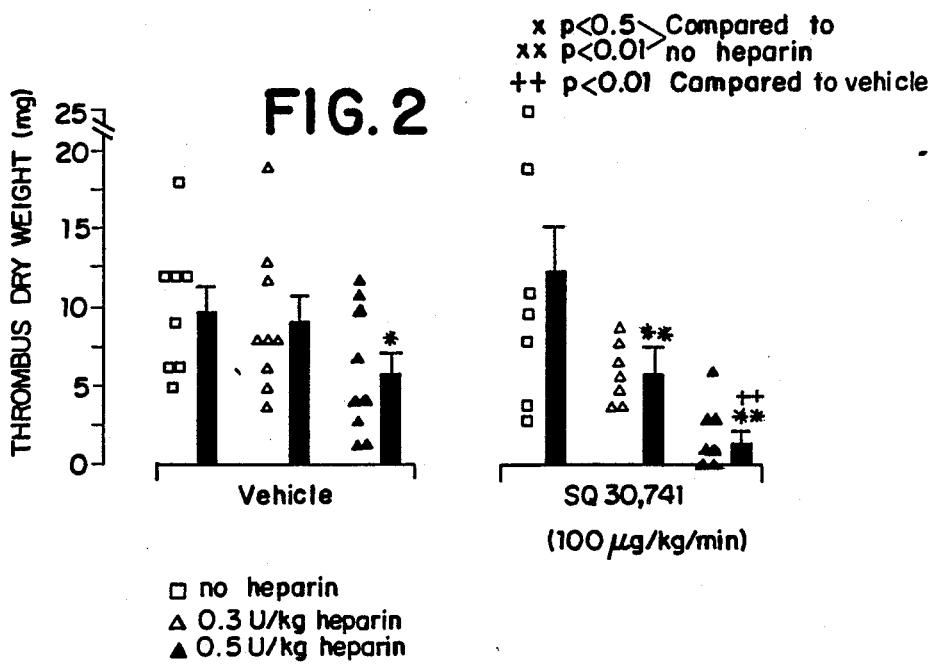

METHOD OF PREVENTING OR REDUCING VENOUS THROMBOSIS USING A THROMBOXANE A₂ RECEPTOR ANTAGONIST IN CONJUNCTION WITH HEPARIN AND COMBINATION

FIELD OF THE INVENTION

The present invention relates to a method for preventing or reducing deep vein thrombosis (DVT), and/or pulmonary embolism, especially following surgery, by administering a thromboxane $A_2$ receptor antagonist with the anticoagulant heparin and to a synergistic combination of thromboxane $A_2$ receptor antagonist and heparin.

BACKGROUND OF THE INVENTION

The use of thromboxane $A_2$ receptor antagonists for arterial thrombosis is well recognized, but their application in venous thrombosis and as adjuncts to heparin is not established. The anticoagulant heparin, which is the choice drug for preventing venous clots, is much less effective in the arterial circulation. Likewise, aspirin and other antiplatelet drugs impede arterial thrombosis, but are generally ineffective against venous thrombosis. This dichotomy exists because of important differences in the mechanisms of clot formation in the venous and arterial arms of the vascular tree. Arterial clots (white thrombus) consist primarily of platelets, which have aggregated in response to vessel injury. Venous clots (red thrombus) differ in that stasis of blood flow and activation of coagulation (plasma thickening) combine with vessel damage to generate a red blood cell rich mass. This is not to say that coagulation is not involved in arterial thrombosis, or that platelets do not have a role in venous clot formation, only that the magnitude of impact differs in each particular instance.

There is indeed room for improvement over the use of heparin for prophylaxis of DVT, especially after total hip replacement (Hampson et al., "Failure of low-dose heparin to prevent deep-vein thrombosis after hip-replacement arthroplasty." Lancet 2:795–797, 1985). Recent therapeutic approaches have focused on combination therapies involving agents selective for the individual components responsible for venous clot formation, which include vessel injury, blood coagulation and blood stasis. It has been suggested that inhibition of two of these three components would maximize the potential for preventing DVT (Comerota et al, "Combined dihydroergotamine and heparin prophylaxis of postoperative deep vein thrombosis; proposed mechanism of action." Am. J. Surgery 150:39–44, 1985). Dihydroergotamine is a vasoactive drug used to increase venous tone and thereby reducing blood stasis in vessels where pooling of blood is a potential thrombotic hazard. Dihydroergotamine has been found to act synergistically with heparin in reducing the incidence of post-surgical DVT (Kakkar et al., "Prophylaxis for postoperative deep-vein thrombosis." JAMA 241:39–42, 1979). A combination of dihydroergotamine and heparin with lidocaine has been marketed by Sandoz (Embolex) for prophylaxis against DVT and pulmonary embolism associated with major abdominal, thoracic or pelvic surgery.

The combination of aspirin with heparin was investigated in venous thrombosis during the 1970's. Some of the results were promising (Vinazzer et al., "Prophylaxis of postoperative thromboembolism by low dose heparin and by acetylsalicyclic acid given simultaneously. A double blind study." Throm. Res. 17:177–184, 1980), although bleeding complications which were associated with the addition of aspirin made this combination unfavorable (Yett et al., "The hazards of aspirin plus heparin." New Eng. J. Med. 298:1092, 1978). The inability to reverse the action of aspirin was no doubt a disadvantage in these studies. In contrast, the activity of the thromboxane $A_2$ receptor antagonist SQ 30,741 would reverse rapidly upon cessation of intravenous administration. There are also theoretical reasons why aspirin might have lesser efficacy when compared to SQ 30,741. Treatment of human platelets with another cyclooxygenase inhibitor was found to cause expression of procoagulant activity (Barrowcliffe et al., "Procoagulant activity of arachidonic acid metabolites." Br. J. Pharmacol. 92:129–132, 1987). This appeared to result from a deleterious diversion of platelet arachidonic acid metabolism into other pathways. Such a reaction or inhibition of beneficial prostaglandins, including prostacyclin, would not be expected with a thromboxane $A_2$ receptor antagonist.

Aspirin may also be effective against pulmonary embolism associated with major surgery (Jennings, J. J., et al., J. Bone Joint Surgery, 58A:926–928, 1976).

It has been found that although thromboxane $A_2$ receptor antagonists (SQ 30,741 and BM 13,505) are capable of reducing venous thrombosis by approximately 50% in rats, this is less than the effect achieved with heparin and required fairly high doses of the $TxA_2$ antagonists. For these reasons $TxA_2$-receptor antagonists alone might not prove to be therapeutically beneficial against DVT.

DESCRIPTION OF THE INVENTION

In accordance with the present invention, a method is provided for preventing or reducing deep vein thrombosis (DVT), especially after surgery, and/or pulmonary embolism, by administering a thromboxane $A_2$ receptor antagonist as an adjunct to heparin, wherein a sub-threshold antithrombotic amount of a thromboxane $A_2$ receptor antagonist is systemically administered, in conjunction with heparin therapy, such as orally, parenterally, transdermally, or by inhalation so as to act synergistically with heparin to prevent, reverse or mitigate venous thrombosis formation.

The term "venous thrombosis" as employed herein refers to deep vein thrombosis and/or pulmonary embolism associated with major abdominal, thoracic or pelvic surgery.

The current low dose heparin for prophylaxis of DVT is 5000 U ("U" is U.S.P. units) given every 8 or 12 hours (Council on Thrombosis, American Heart Association, 1977). It has been found that when employed in combination, the thromboxane $A_2$ receptor antagonist and heparin may each be employed at levels below that required for antithrombotic activity. Thus, either this dose of heparin, or preferably a lower threshold dose of about 1000 to 5000 U every 8 to 12 hours, would be selected for coadministration with the thromboxane $A_2$ receptor antagonist used in an amount within the range from about 0.05 to about 3 mg/kg/hr and preferably from about 0.1 to about 1 mg/kg/hr. Alternatively, comparable or lower activities of a low molecular weight heparin could be used.

Thus, in addition, in accordance with the present invention, a synergistic combination of thromboxane A₂ receptor antagonist and heparin are provided which may be administered for preventing or reducing deep vein thrombosis and/or pulmonary embolism in amounts below the threshold level of effectiveness of each of these components to achieve excellent antithrombotic results. The above combination of the invention may include a weight ratio of thromboxane A₂ receptor antagonist:heparin (100–200 U/mg preparation) of within the range of from about 0.1:1 to about 50:1 and preferably from about 0.5:1 to about 4:1.

The term "thromboxane A₂ receptor antagonist" as employed herein includes compounds which are so-called thromboxane A₂ receptor antagonists, thromboxane A₂ antagonists, thromboxane A₂/prostaglandin endoperoxide antagonists, TP-receptor antagonists, or thromboxane antagonists except insofar as the compound is an inhibitor of thromboxane synthesis but not an antagonist of thromboxane A₂ receptor mediated responses.

Thromboxane A₂ receptor antagonists which may be employed herein include the 7-oxabicycloheptane and 7-oxabicycloheptene compounds disclosed in U. S. Pat. No. 4,537,981 to Snitman et al, especially, [1S-[1α,2β(5Z),3β(1E, 3R,4S),4α]]-7[3-(3-hydroxy-4-phenyl-1-pentenyl)-7-oxabicyclo[2.2.1]hept-2-yl]-5-heptenoic acid; the 7-oxabicycloheptane substituted minoprostaglandin analogs disclosed in U. S. Pat. No. 4,416,896 to Nakane et al., especially, [1S-[1α,2β(5Z),3β,4α]]-7-3-[[2-(phenylamino)carbonyl]hydrazino]methyl]-7-oxabicyclo2.2.1]hept-2-yl]-5-heptenoic acid; the 7-oxabicycloheptane substituted diamide prostaglandin analogs disclosed in U. S. Pat. No. 4,663,336 to Nakane et al, especially, [1S-[1β,2α(5Z)-,3α,4β]]-7-3-[[[[(1-oxoheptyl)amino]acetyl]amino]methyl]-7-oxabicyclo[2.2.1]- hept-2-yl]-5-heptenoic acid and the corresponding tetrazole, and [1S-[1<β,- 2<β(Z),3<β,4<α]]-7-[3-[[[[(4-cyclohexyl-1-oxobutyl)amino]acetyl]amino]methyl]-7-oxabicyclo[2.2.1]hept-2-yl]-5-heptenoic acid; the phenoxyalkyl carboxylic acids disclosed in U. S. Pat. No. 4,258,058 to Witte et al, especially 4-[2-(benzenesulfamido)ethyl]phenoxyacetic acid, (BM 13,177 - Boehringer Mannheim), the sulphonamidophenyl carboxylic acids disclosed in U. S. Pat. No. 4,443,477 to Witte et al, especially 4-[2-4-chlorobenzenesulfonamido)ethyl] phenylacetic acid, (BM 13,505, Boehringer Mannheim) the arylthioalkylphenyl carboxylic acids disclosed in U. S. application Ser. No. 067,199 filed June 29, 1987, especially 4-(3-((4-chlorophenyl)sulfonyl)propyl)benzeneacetic acid.

Other examples of thromboxane A₂ receptor antagonists suitable for use herein include, but are not limited to (E)-5-[[[(pyridinyl)[3-(trifluoromethyl)phenyl]methylene]amino]oxy]pentanoic acid also referred to as R68,070 - Janssen Research Laboratories, 3-[1-(4-chlorophenylmethyl)-5-fluoro-3-methylindol-2-yl]-2,2-dimethylpropanoic acid [(L-655240 Merck-Frosst) Eur. J. Pharmacol. 135(2):193, 17 Mar. 87], 5(Z)-7-([2,4,5-cis]-4-(2-hydroxyphenyl)-2-trifluoromethyl-1,3-dioxan5-yl)heptenoic acid (ICI 185282, Brit. J. Pharmacol 90 (Proc. Suppl):228 P-Abs., Mar. 87), 5(Z)-7-[2,2-dimethyl-4-phenyl-1,3-dioxan-cis-5-yl]heptenoic acid (ICI 159995, Brit. J. Pharmacol. 86 (Proc. Suppl):808 P-Abs., Dec. 85), N,N'-bis[7-(3-chlorobenzeneaminosulfonyl)-1,2,3,4-tetrahydro-isoquinolyl]-disulfonylimide (SKF 88046, Pharmacologist 25(3):116 Abs, 117 Abs, Aug. 83), [1α(Z)-2β,5α]-(+)-7-[5-[[(1,1'-biphenyl)-4-yl]methoxy]-2-(4-morpholinyl)-3-oxocyclopentyl]-4-heptenoic acid (AH 23848 - Glaxo, Circulation 72(6):1208, Dec. 85), GR32191-Glaxo (Thromb. Haemostas, 58 (1) 181 (1987), levallorphan allyl bromide (CM 32,191, Sanofi, Life Sci. 31 (20–21):2261, 15 Nov. 82), (Z,2-endo-3-oxo)-7-(3-acetyl-2-bicyclo[2.2.1-]heptyl-5-hepta-3Z-enoic acid, 4-phenylthiosemicarbazone (EP092 - Univ. Edinburgh, Brit, J. Pharmacol. 84(3):595, Mar. 85).

The disclosure of the above-mentioned patents, patent applications and other references are incorporated herein by reference.

In carrying out the method of the present invention, the thromboxane A₂ receptor antagonist may be administered systemically, such as orally or parenterally or transdermally, to mammalian species, such as monkeys, dogs, cats, rats, humans. Thus, the thromboxane A₂ receptor antagonist may be administered, for example, orally, intravenously, intrapulmonary arterially, intraarterially, transdermally, or by inhalation to provide an initial dosage of from about 0.05 mg/kg to about 3 mg/kg and preferably from about 0.1 mg/kg to about 1 mg/kg. The thromboxane antagonist may be administered (1) before administering heparin, (2) with heparin, or (3) within several minutes after administering heparin.

The thromboxane A₂ receptor antagonist may be incorporated in a conventional dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid or sodium bisulfite) or the like. Parenteral dosage forms are preferred, although oral, transdermal, and aerosol forms are quite satisfactory as well.

With regard to such systemic formulations, single or divided doses of from about 0.5 to about 2500 mg, preferably from about 5 to 2000 mg/one to four times daily, may be administered in systemic dosage forms as described above.

The heparin will normally be administered intravenously or subcutaneously, although other parental dosage forms such as mentioned above with respect to the thromboxane receptor antagonist may be employed as well to provide a dosage of heparin of from about 1000 U to about 5,000 U two to three times daily and preferably from about 2,000 U to about 5,000 U two to three times daily.

FIG. 1 is a graph showing the effect of the TxA₂ antagonists SQ 30,741 and BM 13,505, as well as heparin and control vehicle each used separately, in reducing thrombus size; and FIG. 2 is a graph showing the effect of a combination of the thromboxane antagonist SQ 30,741 and heparin in reducing thrombus size.

The following Examples represent preferred embodiments of the present invention.

EXAMPLE 1

An injectable solution of thromboxane A₂ receptor antagonist for intravenous or intraarterial use with heparin in preventing or reducing deep vein thrombosis and/or pulmonary embolism is produced as follows: [1S-[1β,2α(5Z),3o,4]]-7-[3-[[[[(1oxoheptyl)amino]acetyl]amino]methyl]7-oxabicyclo[2.2.1]hept-2-yl]5-heptenoic acid (SQ 30,741) 2500 mg Methyl paraben 5 mg Propyl paraben 1 mg Sodium chloride 25 g Water for injection qs. 5 l.

The thromboxane A₂ receptor antagonist, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains a concentration of 75 mg of active ingredient per 150 ml of solution.

EXAMPLE 2

An injectable for use in conjunction with heparin in preventing or reducing deep vein thrombosis and/or pulmonary embolism is prepared as described in Example 1 except that the thromboxane $A_2$ receptor antagonist employed is the phenoxyalkyl carboxylic acid 4-[2-(benzenesulfamido)ethyl]phenoxyacetic acid, disclosed in U. S. Pat. No. 4,258,058.

EXAMPLE 3

An injectable solution of thromboxane $A_2$ receptor antagonist for intravenous or intraarterial use in conjunction with heparin and containing [1S-[1α,2β(5Z),3β,4α]]-7-[3-2-(phenylamino)carbonyl]hydrazino]methyl]-7-oxabicyclo[2.2.1]hept-2-yl]-5-heptenoic acid (SQ 29,548) as the thromboxane $A_2$ receptor antagonist is prepared as described in Example 1.

EXAMPLE 4

An injectable for use in preventing or reducing deep vein thrombosis and/or pulmonary embolism is prepared as described in Example 1 except that the thromboxane $A_2$ receptor antagonist employed is [1S-[1<α,-2<β(Z),3<β,4<α]]-7-[3-[[[(4-cyclohexyl-1-oxobutyl)amino]acetyl]amino]- methyl-7-oxabicyclo[2.2.1]hept-2-yl]-5-heptenoic acid.

EXAMPLE 5

A thromboxane $A_2$ antagonist formulation suitable for oral administration and employed as a heparin adjunct is set out below.

1000 tablets each containing 400 mg of thromboxane $A_2$ receptor antagonist are produced from the following ingredients. [1S-[1β,2o(5Z),3α,4β]-7-[3-[[[(1Oxoheptyl)amino]acetyl]amino]methyl]7-oxabicyclo[2.2.1]hept-2-yl]-5heptenoic acid (SQ 30,741) 400 g Corn starch 50 g Gelatin 7.5 g Avicel (microcrystalline cellulose) 25 g Magnesium stearate 2.5 g The thromboxane $A_2$ receptor antagonist and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 400 mg of active ingredient.

EXAMPLES 6 and 7

The following aerosol (inhalation) formulations may be used (in conjunction with heparin) in preventing or reducing deep vein thrombosis and/or pulmonary embolism and may be administered by itself or in conjunction with an inhalation anesthetic.
Specific
Amount Example 6 by Wt. by Wt. SQ 30,471 0.01 to 1 0.05 Ethanol 5-50 25 Freon 11 or 114 50-50 Freon 12 mixture 50-95 74.95 Example 7 by Wt. SQ 30,741 0.01-1 Surfactant (Oleic acid, oleyl alcohol, lecithin) qs. Water qs. Freon 11 or 114 - 50-50 Freon 12 qs. to 100 mixture

EXAMPLE 8

The following experiments were carried out to show that subthreshold doses of thromboxane $A_2$ receptor antagonist and heparin can act synergistically to impede venous thrombosis.

Venous thrombosis was produced in male Sprague-Dawley rats (250 to 300 g) by combination of venous injury, caused by osmotic and pressure stress, and blood stasis. Rats were anesthetized with Na-pentobarbital (30 mg/kg, i.p.) and a PE-50 catheter was inserted into a jugular vein for drug administration. The vena cava was isolated from a midline abdominal incision. A vena cava sac was produced by tieing a ligature around a 26 gauge needle just distal to the renal veins and applying an atraumatic microaneurysm clamp just proximal to the bifurcation of the femoral veins. A separate 26 gauge hypodermic needle was inserted into the inferior portion of the venous sac and hypotonic saline (0.225%) as infused at 10 ml/min for 15 sec. The hypodermic needle was removed from the venous sac following the hypotonic saline flush and the hole was sealed with cyanoacrylate cement. The proximal needle was then slipped free from the ligature, leaving a fixed nonocclusive stenosis, and the distal vascular clamp was removed.

Blood flow was maintained through the stenosis for 20 minutes before reattaching the proximal and distal vascular clamps on the vena cava to redefine the sac. The sac was immediately removed from the rat and slit open lengthwise. The exposed thrombus was placed in a preweighed vial, dried overnight at 60 degrees centigrade, and its weight determined on a Sartorius R-160P balance (Brinkmann Instruments Inc., Westbury, N.Y.). This procedure was modified from Millet and coworkers (Thromb. Res. 45:123–133, 1987) by substituting hypotonic for normal saline during the flushing.

The effect of $TxA_2$-receptor antagonists and heparin on venous thrombosis was examined using the following groups: Vehicle (50 μl/min of a 10% solution of 95% ethanol and 2% $Na_2CO_3$; n=8), SQ 30,741 (50, 100 and 500 μg/kg/min; n=8 per dose), BM 13,505 (50 μg/min/kg; n=7), heparin (Upjohn, Kalamazoo, MI; 50 U/kg; n=6). The effect of SQ 30,741 on the antithrombotic activity of heparin was examined using lower doses of heparin (0.3 and 0.5 U/kg; n=9 per dose) in the presence of either Vehicle or SQ 30,741 (100 μg/kg/min; i.v.). All treatments were given by the i.v. route 15 min before the infusion of hypotonic saline, and infusions were maintained until sac removal. Animals receiving heparin were also given Vehicle infusion.

Treatment group differences were determined by an analysis of variance with mean differences tested by preplanned contrasts. Data were subjected to square root transformations when variances were not homogenous. The analysis was performed using a microcomputer statistics package (Systat, Evanston, IL). A $p<0.05$ was considered significant. All data are expressed as mean ±S.E.

Results

Effect of Heparin and $TxA_2$ antagonists on Venous Thrombosis.

Preliminary experiments demonstrated that both the vena cava stenosis and hypotonic saline flush were required for reproducible thrombus formation. The use of normal saline as originally established by Millet and coworkers, Thromb. Res. 45:123-133, 1987 was not adequate. The selection of hypotonic saline was based on the previously described thrombogenic activity of this stimulus (Hladovec, Thromb. Res. 43:545-551, 1986). When these conditions were met, thrombi were detected in all Vehicle-treated animals with an average weight of 10.0±1.5 mg (FIG. 1). Thrombus formation was clearly abated by antagonism of TxA$_2$-receptors. Thrombus mass was significantly ($p<0.01$) reduced 58% with SQ 30,741 (500 μg/kg/min) and 56% with BM 13,505 (50 μg/kg/min). The extent of this inhibition was the same for two TxA$_2$-antagonists. Lower doses of SQ 30,741 (50 and 100 μg/kg/min) did not alter thrombus formation.

Heparin (50 U/kg) was also efficacious in this model (FIG. 1). Thrombus weights were reduced by an average of 95% ($p<0.001$) and measurable clots were detectable in only half of the animals. This effect exceeded that achieved with either TxA$_2$-antagonist ($p<0.001$).

In order to determine if coadministration of heparin and a TxA$_2$-antagonist would be synergistic, the effect of combining a subthreshold dose of SQ 30,741 with subthreshold and threshold doses of heparin was investigated (FIG. 2). Two treatment groups were constructed; one group received Vehicle (left panel) and the other was given SQ 30,741 (100 μg/kg/min, right panel). Heparin was either omitted (□) or administered at a dose of 0.3 U/kg (Δ) or 0.5 U/kg (▲). In the Vehicle group thrombus mass was not altered by 0.3 U/kg of heparin (Δ), but was reduced 40% by 0.5 U/kg of heparin ( ) ($p<0.05$). In the presence of SQ 30,741 the previously subthreshold dose of 0.3 U/kg of heparin now produced a 50% reduction in thrombus mass ($p<0.01$). This result may be alternatively viewed as a subthreshold dose of SQ 30,741 being enhanced by a subthreshold dose of heparin. The addition of SQ 30,741 also augmented the activity of 0.5 U/kg of heparin to a 87% reduction in thrombus mass ($p<0.01$).

Discussion

The involvement of TxA$_2$-receptor activation in venous thrombosis has been demonstrated by the ability of two structurally unrelated TxA$_2$-receptor antagonists to inhibit thrombus formation by approximately 60%. The extent of TxA$_2$-receptor antagonism required exceeded that which would have ben anticipated based on data obtained for inhibition of arterial thrombosis. SQ 30,741 interrupts occlusive thrombotic cycling of blood flow in stenotic and injured monkey arteries at a threshold i.v. dose of 0.3 mg/kg (Schumacher et al., J. Pharmacol. Exp. Ther. 243:460-466, 1987).

The TxA$_2$-antagonists were less effective when compared to the practically complete elimination of clot formation obtained with heparin. Judging from the low threshold for heparin (0.5 U/kg) this model is highly sensitive to anticoagulants. This indicates a less severe injury as compared to models that combine venous stasis with either a surface activating agent, such as kaolin (Hladovec, Physiol. Bohemo S/DV, 24:551-554, 1975), or activated plasma (Wessler, 1962). In addition to their individual activities, heparin and SQ 30,741 function synergistically. This is demonstrated by the 50% reduction in thrombus mass achieved when SQ 30,741 and heparin were combined at doses which lacked antithrombotic activity individually. SQ 30,741 also potentiated the effect of a threshold dose of heparin from 40 to 87% inhibition of clot formation. These data indicate that a TxA$_2$-antagonist could be useful clinically as an adjunct for lowering heparin load and in combination with heparin could be useful in treating thrombophlebitis or pulmonary embolism associated with DVT.

What is claimed is:

1. A method for preventing or reducing deep vein thrombosis, pulmonary embolism or both in a mammalian species, which comprises administering to a mammalian species in need of such treatment an effective amount of a thromboxane A$_2$ receptor antagonist and an effective amount of heparin, wherein the thromboxane A$_2$ receptor antagonist is employed in a weight ratio to the heparin of within the range of from about 0.1:1 to about 50:1.

2. The method as defined in claim 1 wherein the thromboxane A$_2$ receptor antagonist is administered systemically.

3. The method as defined in claim 1 wherein the thromboxane A$_2$ receptor antagonist is administered intravenously, orally, intraarterially, intrapulmonary arterially, transdermally, or by inhalation.

4. The method as defined in claim 1 wherein the thromboxane A$_2$ receptor antagonist is administered before, during or within several minutes after the administration of heparin.

5. The method as defined in claim 1 wherein the thromboxane A$_2$ receptor antagonist is administered during administration of heparin.

6. The method as defined in claim 1 wherein the thromboxane A$_2$ receptor antagonist is a 7-oxabicycloheptane or a 7-oxabicycloheptene.

7. The method as defined in claim 1 wherein the thromboxane A$_2$ receptor antagonist is a 7-oxabicycloheptane substituted amino-prostaglandin analog.

8. The method as defined in claim 1 wherein the thromboxane A$_2$ receptor antagonist is a 7-oxabicycloheptane substituted diamide prostaglandin analog.

9. The method as defined in claim 1 wherein the thromboxane A$_2$ receptor antagonist is a phenoxyalkyl carboxylic acid.

10. The method as defined in claim 1 wherein the thromboxane A$_2$ receptor antagonist is a sulfonamidophenyl carboxylic acid.

11. The method as defined in claim 1 wherein the thromboxane A$_2$ receptor antagonist is an arylthioalkylphenyl carboxylic acid.

12. The method as defined in claim 1 wherein the thromboxane A$_2$ receptor antagonist is [1S-[1α,2β(5Z), 3β(1E,3R,4S),4α ]]-7-[3-(3-hydroxy-4-phenyl-1-pentenyl)-7-oxabicyclo[2.2.1]hept-2-yl]-5-heptenoic acid.

13. The method as defined in claim 1 wherein the thromboxane A$_2$ receptor antagonist is [1S-[1β,2α(5Z)-,3α,4β]]-7-[3-[[[[(1-oxoheptyl)amino]acetyl]amino]methyl]-7-ox acid or the corresponding tetrazole.

14. The method as defined in claim 1 wherein the thromboxane A$_2$ receptor antagonist is [1S-[1<α,-2<β(Z) ,3<β,4<α]]-7-[3-[[[[(4-cyclohexyl-1-oxobutyl)-amino]ace acid.

15. The method as defined in claim 1 wherein the thromboxane A$_2$ receptor antagonist is [1S-[1α,2β(5Z),3β,4α]]-7-[3-[[2-(phenylamino)carbonyl]-hydrazino]methyl]-7-[3 hydrazino]methyl-7-oxabicyclo[2.2.1]hept-2-yl]-5-heptenoic acid.

16. The method as defined in claim 1 wherein the thromboxane A$_2$ receptor antagonist is 4-(3-((4-chlorophenyl)-sulfonyl)propyl acetic acid.

17. The method as defined in claim 1 wherein the thromboxane A$_2$ receptor antagonist is 4-[2-(benzenesulfamido)-ethyl]phenoxy acid or 4-[2-(4-chlorobenzenesulfonamido)-ehtyl]phenylacetic acid.

18. A pharmaceutical combination for preventing or reducing deep vein thrombosis, pulmonary embolism or both, comprising a thromboxane A₂ receptor antagonist and heparin, employed in a weight ratio to each other of within the range of from about 0.1:I to about 50:1.

19. The combination as defined in claim 18 wherein the thromboxane A₂ receptor antagonist is present in a weight ratio to heparin of within the range of from about 0.5:1 to about 4:1.

20. The combination as defined i claim 19 wherein the thromboxane A₂ receptor antagonist is [IS-[1β,2α(5Z)-,3α,4β]]-7-[3-[[[[(1-oxoheptyl)amino]acetyl]amino]methyl]-7-oxabicyclo[2.2.1]hept-2-yl]-5-heptenoic acid or the corresponding tetrazole.

* * * * *